United States Patent
Strasser et al.

(10) Patent No.: US 6,521,460 B1
(45) Date of Patent: Feb. 18, 2003

(54) METHOD OF CARRYING OUT BLOOD TESTS

(75) Inventors: Alexander W. M. Strasser, Duesseldorf (DE); Karl Melber, Duesseldorf (DE); Hans Dietrich Menssen, Berlin (DE); Eckard Thiel, Berlin (DE)

(73) Assignee: Rhein Biotech Gesellschaft fur Neue Biotechnologische Prozesse und Produkte mbH (DE)

( * ) Notice: Subject to any disclaimer, the term of this patent is extended or adjusted under 35 U.S.C. 154(b) by 0 days.

(21) Appl. No.: 09/180,806

(22) PCT Filed: May 7, 1997

(86) PCT No.: PCT/EP97/02343

§ 371 (c)(1),
(2), (4) Date: Feb. 8, 1999

(87) PCT Pub. No.: WO97/44661

PCT Pub. Date: Nov. 27, 1997

(30) Foreign Application Priority Data

May 21, 1996 (DE) ......................... 196 20 443

(51) Int. Cl.[7] .............................. G01N 33/86
(52) U.S. Cl. ............... 436/69; 436/18; 436/63; 436/66; 422/73; 600/369
(58) Field of Search .................. 436/17, 18, 63, 436/66, 69, 176; 422/57, 68.1, 73, 102; 600/368, 369

(56) References Cited

U.S. PATENT DOCUMENTS 5,187,102 A * 2/1993 Stocker et al. ................ 436/69

FOREIGN PATENT DOCUMENTS

| DE | 43 29 969 A1 | 3/1995 |
| EP | 0 442 843 A1 | 8/1991 |
| WO | WO92/14150 | 8/1992 |
| WO | WO96/10749 | 4/1996 |

OTHER PUBLICATIONS

Walsman (1988) Die Pharmazie 43:737.

Derwent AN 92–34543 for JP4249766, 1992.

Sterling et al. (1992) Clin. Chem. 38:1658.

W. Rick, "Klinische Chemie und Mikroskopie", Springer–Verlag Berlin Heidelberg New York, 1977, (2 pages).

Clinical Laboratory Medicine Fifth Edition, Richard Ravel, Library of Congress Cataloging in Publication Data, 1932, 14 pages.

* cited by examiner

Primary Examiner—Maureen M. Wallenhorst
(74) Attorney, Agent, or Firm—Swanson & Bratschun, LLC

(57) ABSTRACT

The present invention relates to a method of carrying out blood tests. The invention is based on the finding that clinico-chemical blood parameters can be determined using not only blood serum but also blood plasma. Therefore, freshly taken blood samples, which are mixed with at least one thrombin inhibitor, can be used for determining both clinico-chemical parameters and hematological parameters. The clinico-chemical parameters can thus be determined using blood plasma, a separation of coagulable components being not required any more.

21 Claims, No Drawings

METHOD OF CARRYING OUT BLOOD TESTS

FIELD OF THE INVENTION

The present invention relates to a method of carrying out blood tests.

BACKGROUND OF THE INVENTION

Many diverse blood tests are required for diagnosing, in particular, internal diseases and for controlling the course thereof. These blood tests can be divided into tests regarding the cellular blood components (blood count, differential blood count, blood group, immunophenotyping of blood cells) and into serum tests and also into antibody screening tests, Coombs tests and cross-matching tests. Serum tests are concerned with the determination of enzymes, metabolic products (e.g. creatinine, urea, blood sugar) and coagulation parameters. In addition, special tests, such as hormone analyses or drug level analyses, are carried out on the basis of serum.

With seriously ill and hospitalized grown-up patients, enlarged blood tests have to be carried out over a prolonged period of time every day and sometimes even twice a day to detect critical changes in the physical condition of the patient at an early stage. Blood is taken under sterile conditions normally using a closed blood taking system by puncturing a vein in the bend of the elbow (e.g. V. cubita mediana). Blood is optionally taken through already laid central indwelling catheters. Depending on the clinical requirements and the desired laboratory tests, types and numbers of the tubes to be filled with blood are defined. Specific laboratory tests can only be carried out with specific substances specifically prepared for such tests (e.g. specific anticoagulants (heparin, EDTA, citrate, etc.)) or with glucosidase inhibitor ("blood sugar tubes") or blood withdrawing tubes containing coagulation-promoting substances ("serum tubes"). Heparin and EDTA are unspecific, indirect inhibitors. They do not act directly or specifically on a specific element of the blood coagulation cascade, but their effect is of an indirect nature in that they intercept, for example, $Ca^{2+}$ ions which, in turn, are essential for the activation of different proteins of the coagulation system. A uniform pretreatment of the blood to be tested ("standard tube"), on the basis of which all or at least the majority of important blood tests could then be carried out, does not exist. Furthermore, it follows from the standard logistic sequence in clinico-chemical or hematological laboratories that a plurality of blood withdrawal tubes that have been pretreated in the same way are often needed. After withdrawal from the patient, and depending on the laboratory values to be determined, the blood tubes are transferred into laboratories that are most of the time separated spatially (most of the time a clinico-chemical laboratory and a hematological laboratory and optionally laboratories for special tests, such as immunophenotyping, drug level in the serum, etc. (material dispatch by mail or courier might here be necessary). The blood tubes received in the laboratory must first be sorted, and the tubes to be centrifuged are then centrifuged at about 3,500 r.p.m. for five minutes. The blood taking tubes are then forwarded to the different work places (coagulation tubes to the coagulation place, serum tubes for electrolyte determination on the flame photometer, etc). The respective automatic analyzing devices are then loaded with the samples, with the sample volume of about 10 μl to 100 μl, which is needed for one measurement, being very small in most measuring operations. The actual measuring operation lasts from a few seconds to a few minutes (five minutes at the most, depending on the method and the device). The measured values are finally printed out and, depending on the origin, are communicated in writing to the dispatching stations.

In summary, it is necessary at the moment that several blood taking tubes (depending on the desired test) should be filled with 2–10 ml blood (depending on the tube size) in a blood taking process. The following tubes are needed for determining the routine laboratory parameters:

| | |
|---|---|
| blood count and differential blood count | 1 × EDTA tube |
| sodium, potassium in the serum | 1 × serum tube |
| liver enzymes and/or creatinine and/or urea and/or lipase and amylase and/or creatinine kinase and/or cholesterol and triglycerides and/or lactate dehydrogenase | 1 × serum tube |
| total protein and protein electrophoresis | 1 × serum tube |
| glucose in the serum | 1 × glucose tube |
| Quick, PTT | 1 × coagulation tube (citrate) |
| blood sedimentation rate | 1 × BSR tube |
| total | 7 tubes |

If, in addition, the blood group has to be determined and an antibody screening test has to be carried out and erythrocyte concentrates have to be provided for, two further blood taking tubes (without additions) have to be taken. In the case of special tests that are required, e.g. hormone level analyses (T3, T4, TSH basal, etc.), drug level (digitoxin level, vancomycin level, theophylline level, etc.), special electrolyte concentrations (magnesium, calcium, phosphate) and special coagulation values (deficiency in factors, fibrin degradation products), and many others, an additional withdrawal tube (most of the time serum tube) is needed for each test as a rule.

Hence, independently of the blood taking system, the following serious drawbacks are found in these blood taking methods that have so far been in general use:

1. The daily blood withdrawals which must be performed in the case of seriously ill patients lead to a blood loss of about 250 ml per week. This is an amount approximately half the blood donation amount of a healthy person at the German Red Cross. Another drawback is that seriously ill persons often suffer from anemia caused by very different factors.
2. The many blood withdrawing operations that are required are a considerable cost factor in medical care; on the one hand, because of the purchasing costs and, on the other hand, because of the considerable disposal costs for the tubes. The blood tubes used are classified as infectious wet waste and must be burnt being packed in special containers. In the case of seriously ill persons about 40 blood taking tubes are needed every week.
3. The workplace classification which is defined and segmented by the differently pretreated blood samples (anticoagulated whole blood for blood count determination, serum for enzyme tests and electrolyte determinations, etc.) and by the automatic measuring devices adapted thereto requires a multitude of work places entailing correspondingly high costs with respect to personnel and financing.

SUMMARY OF THE INVENTION

It is the object of the present invention to provide a method for carrying out blood tests, whereby the above-mentioned drawbacks can be overcome and many blood measuring parameters can be determined rapidly and reliably within a short time interval almost at the same time.

This object is achieved by a method according to claim 1. The achievement of such an object is, in particular, due to the finding that almost all of the clinico-chemical blood parameters can be determined using not only blood serum, but also blood plasma provided such blood plasma—in contrast to standard practice—has been prepared by adding a thrombin inhibitor, such as hirudin. The difference between serum and plasma is that the first one is free from fibrin whereas the latter still contains fibrinogen. Surprisingly enough, it has been found that one and the same blood sample can be used for determining both clinico-chemical parameters and hematological parameters provided the sample is mixed with a thrombin inhibitor. Preferably, hirudin and/or desulfatohirudin is/are used as thrombin inhibitor. This method can be carried out in an automated manner.

Hirudin is a highly specific thrombin inhibitor which is naturally found in the salivary gland secretion of leeches, Hirudo medicinalis. The anticoagulative activity in salivary gland secretions of Hirudo medicinalis was described by Haycraft for the first time about 100 years ago (Haycraft, J. B. (1894), Naunyn-Schmiedebergs Arch. Exp. Pathol. Pharmakol. 18, 209). In the fifties Markwardt et al. succeeded in obtaining hirudin in pure form and in characterizing it biochemically (Markwardt, F. and Walsmann, P. (1958), Hoppe-Seyler's Z. physiol. Chemie 312, 85). Hirudin is a polypeptide of which various, naturally occurring variants have become known in the meantime and which has a molecular weight of about 7000 Dalton. Natural hirudin is used as a thrombin inhibitor for biochemical studies (Walsmann et al., (1988) Pharmazie 43, 737). The use of hirudin has been limited to a very small number of very special applications because of the small hirudin amounts found in leeches and because of the troublesome extraction of hirudin. Among other things, hirudin has also been suggested for the anticoagulation of blood samples for determining the function and change in state of blood cells (e.g. blood sedimentation rate) (EP-A-442 843).

Since the end of the eighties it has been possible to prepare desulfatohirudin by genetic engineering techniques using yeasts or bacteria in great amounts. This recombinant desulfatohirudin is identical with the natural hirudin of Hirudo medicinalis (except for a missing sulfate group on tyrosine 63) and has the same anticoagulant characteristics. On account of the production costs, which are still high, recombinant hirudin is preferably developed for use in the therapeutic field. Its yield, however, could be increased by the use of novel expression systems, such as the yeast Hansenula polymorpha, to an extent (Weydemann et al. (1995), Appl. Microbiol. Biotechnol 44, 377) that non-therapeutical applications present themselves for hirudin. Recombinant desulfatohirudin is easily soluble and can already inhibit blood coagulation in small concentrations. This makes it possible to supply recombinant desulfatohirudin either in dissolved form or as a dry substance and thereby to effectively inhibit blood coagulation. The amount of the supplied desulfatohirudin can be dosed such that the blood taken remains incoagulable, depending on the time required by corresponding tests. Furthermore, the amount of desulfatohirudin can be proportioned such that there will be no dilution effects on the blood volume to be taken and the measurement result will thus not be influenced. The observation of standard volumes is a critical factor in the use of citrate solution as anticoagulant. In contrast to Na-EDTA or citrate solution, the anticoagulating effect in desulfatohirudin is not due to the withdrawal of $Ca^{2+}$ ions, but to a specific steric thrombin inhibition. As a result, no bivalent cations are removed from the blood, which permits an examination of cellular blood components under physiological conditions. Moreover, desulfatohirudin does not require any endogenous factors for its anticoagulative activity, as is e.g. the case with heparins. For instance, heparin requires the factors antithrombin III and heparin cofactor 2 for efficiently inhibiting coagulation. With desulfatohirudin, blood samples that are derived from patients suffering from a corresponding factor deficiency can be analyzed without any additional measures and without any problems. It can be expected because of theoretical considerations that natural hirudin variants and hirudin fragments, as far as they have a thrombin-inhibiting effect, produce the same results as have been obtained for recombinant desulfatohirudin. Furthermore, synthetic thrombin inhibitors can be used with the same result.

When hematological parameters are examined, the blood cells must be vital at the time of examination. The blood must be anticoagulated and must not be changed in its volume parts by the course of the examination; otherwise, the numerical values would be distorted. Hematological test parameters are, e.g., the number of erythrocytes, leukocytes and thrombocytes per volume unit of whole blood, the proportionate composition of the leukocytes from the various nucleated blood cells which is determined under morphological criteria (differential blood), and the degree of loading of the individual erythrocytes with hemoglobin (quotient from the clinico-chemical measurement value hemoglobin concentration and the number of individual erythrocytes per volume unit). Further hematological measurement parameters using immunological test reactants describe the surface property (antigenity) of intact erythrocytes (transfusion-serological tests, cross-matching of conserved blood) or mononuclear blood cells (immunopnehotyping for diagnosing e.g. malign blood diseases). All of these hematological tests have in common that they can only be carried out on undestroyed, vital blood cells.

Hematological measurement parameters are determined either manually by microscope (e.g. by means of a counting chamber for determining the number of blood cells; blood smear preparation for assessing the cell morphology (cell size, nucleus shape, cytoplasma characteristics, cytoplasmatic granulation, etc.)) or in automatic blood-cell counting devices (e.g. Coulter counter). The determination of the hemoglobin value in blood is a clinico-chemical and not a hematological measurement parameter.

The present method is a method which can operate in an automated manner with whole human blood in a blood taking tube in a novel manner and in such an anticoagulated fashion that the blood sample can simultaneously be used for the automated determination of hematological, clinico-chemical and immunological measurement parameters, i.e. in short, for the determination of almost all measurement parameters. The routine measurement methods which have so far been in use can be employed entirely or after having been slightly adapted to the novel anticoagulant.

Furthermore, it should be noted that a quantitative determination by means of automatic measuring devices is possible according to the present method. Fresh capillary blood is used for a manual determination, e.g. in the counting of blood corpuscles. In large laboratories hematological tests, however, can no longer be carried out manually, but only by automated measuring devices. For this purpose venous K2-EDTA-anticoagulated whole blood is resorted to. Thanks to the addition of the anticoagulant dipotassium-ethylenediaminetetraacetic acid (K2-EDTA) in the worldwide standard concentration of 1 mg per 1 ml of blood, a high concentration of potassium ions is introduced into the blood sample, apart from the desired complexation of the calcium ions by the EDTA. Such an artificially high potassium concentration effects a change in the osmotic gradient for potassium between the leukocytes (granulocytes and lymphocytes) and the ambient aqueous environment, with the effect that the leukocytes lose cell water and shrink. After some time (30 minutes) a new osmotic gradient for potassium ions is obtained through compensation mechanisms of the leukocytes, and the cells recover part of the lost cell water. This new equilibrium remains stable for several hours. Of course, it is different in comparison with the native blood which has no K2-EDTA added thereto. It is only when the nucleated blood cells in K2-EDTA-anticoagulated blood have been adapted to this new equilibrium and have reached a shrunken, but stabilized form, that they can be counted in repeatable form in automated measuring devices and can reliably be distinguished from one another in volume, conductivity and stray-light characteristics (automated differential blood counting). An effect similar to the K2-EDTA sample pretreatment is not observed with hirudin, which seems to rule out the use of hirudin blood for automated measurements. Surprisingly enough, however, the present results show that quantitative hematological measurement parameters can be determined in automated measuring devices with hirudin-anticoagulated blood.

When hematological routine parameters, such as the number of erythrocytes, leukocytes and thrombocytes, are determined in an automated manner, the anticoagulants sodium citrate, sodium oxalate and heparin lead to wrong measurement results, which is generally known. The addition of sodium citrate or sodium oxalate to whole human blood will shrink the erythrocytes to such a considerable extent that the situation prevailing in the non-anticoagulated native blood cannot be inferred from the automated size determination of the erythrocytes and the calculated results, e.g. hematocrit. Moreover, when sodium citrate-anticoagulated blood is used, the numerical value of all of the blood cells measured and of the hemoglobin value must be corrected by the factor 1.1. What is even more disadvantageous is the fact that the numerical values of the blood cells vary at random, which could so far not be explained in a satisfactory manner, with the variations having a range of 10% in the case of thrombocytes and, in pathologically reduced thrombocyte values, even a greater range. When heparin-anticoagulated blood is used, unforeseeable, random spontaneous aggregations of thrombocytes and leukocytes may occur, so that during counting in automatic measuring devices partly falsely low measured values are determined for these cells. When anticoagulants, such as heparin, calcium citrate, but also K2-EDTA, are used, such measurement errors are above all observed in the determination of hematological parameters when during the automatic differentiation in the hydrodynamically focused sample flow, the leukocytes are differentiated according to volume (resistance measurement in direct current), conductivity (measurement of the internal conductivity of the cells with high-frequency alternating current) and stray-light characteristics (measurement of the typical surface structures of the cells and their peripheral granulation with a helium-neon laser) (automated differential blood counting). For instance, a heparin addition during automatic differential blood counting is, in particular, detrimental to an exact recognition of the basophilic granulocytes which are rather rare, but particularly important from a diagnostic point of view. Typically, an excessively high value of basophilic granulocytes is indicated. Moreover, such a wrongly determined blood count based on the heparin-anticoagulated whole blood is difficult to be checked manually, such a check, however, being imperative. On account of its great molecular electrostatic charge, the heparin addition interferes with the necessary stains (May-Grünwald stain and Giemsa stain) with which the blood cells which have been smeared on an object carrier of glass are fixed and stained (panoptic staining according to Pappenheim). Thus, the addition of heparin effects a blue tinge of the nucleated blood cells, which makes it difficult or even impossible to distinguish the blood cells by microscope. Finally, serious measurement errors may even be caused by the K2-EDTA which is recommended and used worldwide for determining hematological routine parameters in automated measuring devices, but also in the case of manual determinations. It often happens that small blood clots are formed for the reason that the K2 EDTA-coated blood tubes are not immediately tilted and moved after the withdrawal of blood. Such partly clotted blood samples must not be processed, for they lead to wrong numerical values of the blood cells in the case of determining operations carried out by machine or manually. Moreover, they might clog the microcapillaries of the automatic measuring devices.

Since these many undesired interferences of the different substances for the anticoagulation of whole human blood have been known and could not be foreseen in detail upon the introduction of such substances, it could be assumed that hirudin-anticoagulated whole blood would also interfere in a disadvantageous manner with some of the important routine measurement methods. Therefore, there was some general prejudice among the experts that the determination of a multitude of clinico-chemical parameters and hematological parameters on the basis of a single blood withdrawal vessel is not possible.

With the method according to the invention, however, all of the relevant clinico-chemical and hematological values can be determined from a single blood withdrawal container at the same time. Possible blood value determinations comprise:

1. Determination of the serum parameters (e.g. alkaline phosphatase, amylase, cholinesterase, creatine kinase, GOT, GPT, γ-GT, HBDH, lactate, LDH, lipase, albumin, bilirubin, calcium, chloride, cholesterol, creatinine, iron, total protein, glucose, uric acid, urea, potassium, magnesium, sodium, triglycerides, C-reactive protein, immunoglobulins, transferrin, anti-streptolysin-O, rheumatoid factors, C3, C4, apolipoprotein, drug level). A determination is preferably carried out in automated measuring devices after separation of the corpuscular components from the whole blood. For a further simplification of the method the serum parameters can also be determined in automated measuring devices in which a separation of the corpuscular components is no longer required.
2. Examination of the blood count: partial blood count (automated) and differential blood count (manual and automated).
3. Determination of the blood group, carrying out antibody screening tests, carrying out Coombs tests and cross-matching erythrocytes concentrates.
4. Immunophenotyping of normal and malign mononuclear cells in blood and bone marrow.

A blood withdrawal tube (universal standard tube) which can be used for the present invention may be a blood withdrawal vessel that contains the thrombin inhibitor as a solution or as a dry substance or as a surface coating. The amount of the thrombin inhibitor should be proportioned such that for a period of time in which all of the above-described analyses can be carried out, the coagulation of the withdrawn blood volume is fully inhibited, thereby permitting a conduction of the measurements in the illustrated method without any problems. For instance, tubes, syringes, pipettes and capillaries of plastic material, glass or metal are suited as blood withdrawal vessels.

A further embodiment of the present invention is concerned with the performance of the blood test with automated measuring devices that combine the following functions in one unit:

determining all clinico-chemical parameters,
determining all hematological parameters, wherein in the course of the measuring operation first the hematological values (blood count/differential blood count) should be recorded and then, following a selective removal of the cellular blood components (=hirudin plasma), the clinico-chemcial parameters (including special determinations) should be determined. The cellular components can e.g. be removed via a microfilter or by centrifugation. Furthermore, the above-described blood withdrawal vessels can also be used with measuring devices which carry out determining operations by means of test strips.

It is a further object of the present invention to provide a method of determining clinico-chemical blood parameters It is advantageous to use hirudin and/or desulfatohirudin, preferably recombinant hirudin and/or desulfatohirudin, as the thrombin inhibitor.

In this method, too, the freshly taken blood sample should be put into a withdrawal vessel in which the thrombin inhibitor is provided.

The clinico-chemical parameters can be determined by means of an automated measuring device.

DETAILED DESCRIPTION OF THE INVENTION

The present invention shall be explained in more detail with reference to the following examples:

EXAMPLE

1. It could be shown that the use of recombinant hirudin of the company Rhein Biotech, Düsseldorf, made whole human blood incoagulable in blood taking tubes for differently long periods of time in proportion to the hirudin amount used. At a concentration of 200 ATU rhirudin (=20 ng rhirudin) per ml whole blood the blood was incoagulable for 24 hours; at a concentration of 100 ATU rhirudin (=10 ng rhirudin) the whole blood clotted entirely in glass or plastic withdrawal tubes already after 12 hours (see Table 1).

TABLE 1

Recombinant hirudin as an anticoagulant of whole human blood

Coagulation in hours after addition of the anticoagulant to the fresh whole blood of healthy test persons

| Hirudin in ATU/ml | 0.5 test persons | | | 2 | | | 4 | | | 8 | | | 12 | | | 16 | | | 20 | | | 24 | | | 48 | | |
|---|---|---|---|---|---|---|---|---|---|---|---|---|---|---|---|---|---|---|---|---|---|---|---|---|---|---|---|
| | SP | JR | HM | SP | JR | HM | SP | JR | HM | SP | JR | HM | SP | JR | HM | SP | JR | HM | SP | JR | HM | SP | JR | HM | SP | JR | HM |
| 0 | + | + | + | + | + | + | + | + | + | + | + | + | + | + | + | + | + | + | + | + | + | + | + | + | + | + | + |
|  |  |  |  | + | + | + | + | + | + | + | + | + | + | + | + | + | + | + | + | + | + | + | + | + | + | + | + |
| 10 | + | + | + | + | + | + | + | + | + | + | + | + | + | + | + | + | + | + | + | + | + | + | + | + | + | + | + |
|  |  |  |  |  | + | + | + | + | + | + | + | + | + | + | + | + | + | + | + | + | + | + | + | + | + | + | + |
| 50 | + | + | + | + | + | + | + | + | + | + | + | + | + | + | + | + | + | + | + | + | + | + | + | + | + | + | + |
|  |  |  |  | + | + | + | + | + | + | + | + | + | + | + | + | + | + | + | + | + | + | + | + | + | + | + | + |
| 75 | − | − | − | + | + | + | + | + | + | + | + | + | + | + | + | + | + | + | + | + | + | + | + | + | + | + | + |
|  |  |  |  |  |  |  |  |  | + |  | + | + | + | + | + | + | + | + | + | + | + | + | + | + | + | + | + |
| 100 | − | − | − | − | − | − | + | + | + | + | + | + | + | + | + | + | + | + | + | + | + | + | + | + | + | + | + |
|  |  |  |  |  |  |  |  |  |  |  |  |  | + | + | + | + | + | + | + | + | + | + | + | + | + | + | + |
| 150 | − | − | − | − | − | − | − | − | − | − | + | − | − | + | − | + | + | + | + | + | + | + | + | + | + | + | + |
|  |  |  |  |  |  |  |  |  |  |  |  |  |  |  |  |  |  |  |  |  |  |  |  | + | + | + | + |
| 200 | − | − | − | − | − | − | − | − | − | − | − | − | − | − | − | − | − | − | − | − | − | − | − | − | + | + | − |
| 250 | − | − | − | − | − | − | − | − | − | − | − | − | − | − | − | − | − | − | − | − | − | − | − | − | − | + | − |
| 500 | − | − | − | − | − | − | − | − | − | − | − | − | − | − | − | − | − | − | − | − | − | − | − | − | − | − | − |
| 750 | − | − | − | − | − | − | − | − | − | − | − | − | − | − | − | − | − | − | − | − | − | − | − | − | − | − | − |
| Heparin 5 IE/ml | − | − | − | − | − | − | − | − | − | − | − | − | − | − | − | − | − | − | − | − | − | − | − | − | − | − | − | which can be carried out in a more simple and faster manner than known methods.

This object is achieved by a method set forth in claim 10. Surprisingly enough, it has been found that a freshly taken blood or bone marrow sample which is mixed with a thrombin inhibitor can be used for determining the above-mentioned clinico-chemical parameters. A separation of fibrinogen is not necessary. Preferably, however, the cellular and corpuscular components, as described above; can be separated from the blood plasma prepared in this manner.

Directly after withdrawal, 2 ml whole blood from three healthy test persons (SP, JR, HM) was introduced into non-prepared glass tubes of the Vacutainer blood withdrawal system (company Becton and Dickinson) which had previously been loaded with different amounts of recombinant hirudin. The stock solution of the recombinant hirudin was $10^4$ ATU per ml, so that between 20 µl and 150 µl of the stock solution were used per tube. 5 IE/ml heparin was used as a positive control. The tubes were permanently moved on a roller. The time up to the occurrence of small clots having a diameter of about 1–2 mm (beginning coagulation (+)) and the time up to the occurrence of a complete coagulation (++)

was measured. The presence of microclots inside the blood tubes, with the microdots being unfavorable for the cell-number measuring operation and distorting the result, was checked by repeatedly counting the cells by means of the STKS device of the company Coulter. The detection of microclots was evaluated as a beginning coagulation (+). In cases were no macro- or microclots were detectable, the anticoagulated blood could be analyzed in the STKS of Coulter without any problems (−).

2. It was shown that after centrifugation of the corpuscular elements a multitude of clinico-chemical laboratory assays could be carried out on automated measuring devices without any problems and in a repeatable manner on the basis of blood withdrawal tubes of glass that had been loaded with 200 ATU rhirudin per ml blood. The measured values which were determined and existed in the pathological as well as in the standard range were statistically not significantly different from the values obtained with the conventional method (serum method). Technical problems on the measuring devices, such as clogging of the suction capillaries, etc., occurred seldom and not more frequently than in the serum method. The following measurement parameters were determined in an automated manner: GOT, GPT, alkaline phosphatase, gamma-GT, sodium, potassium, creatinine, urea, creatine kinase, bilirubin, lactate dehydrogenase, alpha-HBDH, amylase, lipase, glucose, total cholesterol, triglycerides, chloride, magnesium, phosphate, calcium, iron, total protein, protein electrophoresis, antistreptolysin titer, C-reactive protein, beta-HCG (see Table 2).

TABLE 2

| test person M parameter | serum | hirudin plasma | unit |
|---|---|---|---|
| GOT/ASAT | 9 | 9 | U/l |
| GPT/ALAT | 10 | 10 | U/l |
| AP | 103 | 100 | U/l |
| GGT | 10 | 10 | U/l |
| HBDH | 96 | 98 | U/l |
| total bilirubin | 12.7 | 13 | µmol/l |
| CK | 60 | 59 | U/l |
| lipase | 79 | 82 | U/l |
| LDH | 166 | 167 | U/l |
| amylase | 75 | 73 | U/l |
| creatinine | 94 | 88 | µmol/l |
| urea | 6.6 | 6.4 | mmol/l |
| total cholesterol | 4.7 | 4.7 | mmol/l |
| triglycerides | 1.6 | 1.6 | mmol/l |
| glucose | 5.3 | 5.5 | mmol/l |
| calcium | 2.22 | 2.19 | mmol/l |
| magnesium | 0.7 | 0.73 | mmol/l |
| phosphate | 1.2 | 1.1 | mmol/l |
| iron | 20 | 20.1 | µmol/l |
| potassium | 4.2 | 3.8 | mmol/l |
| sodium | 142 | 141 | mmol/l |
| chloride | 106 | 108 | mmol/l |
| osmolality | 276 | 278 | mosmol/kg |
| total protein | 76 | 77 | g/l |
| electrophoresis | | | |
| albumin | 70.6 | 67.3 | % |
| alpha 1 | 2.2 | 2.1 | % |
| alpha 2 | 5.3 | 5.8 | % |
| beta | 9.5 | 11.2 | % |
| gamma | 12.4 | 13.6 | % with gradients! |
| AST | <80 | 120 | kU/l |
| CRP | <6 | <6 | mg/l |
| HCG | <2 | <2 | U/l |

3. It was shown that, on the basis of the same hirudin-treated blood taking tubes of glass, a partial blood count (measurement and calculation of the cellular amounts in the whole blood) could additionally be performed on automatic measuring devices and a differential blood count could be made on automatic devices and by hand. The measured values which were found and which were within the pathological and the normal range were statistically not significantly different from the values obtained in the routine method (EDTA blood). Technical problems on the automated cell counting devices (Coulter, USA), such as clogging of the suction cannula or R-alarm (registration error), did not occur often and not more frequently than in the standard method (EDTA blood). For a correct automatic determination of the differential blood count of rhirudin-anticoagulated whole blood, however, the automatic measuring devices which are set to EDTA-anticoagulated blood must be adjusted accordingly to the use of rhirudin-anticoagulated blood. Granulocytic cells, in particular, shrink and thus change due to the EDTA addition within the first 60 minutes. This has the effect that the determination of the automated differential blood count of EDTA blood, e.g. on the STKS device of Coulter, will only be reliable if prior to testing the blood is EDTA-anticoagulated for a period of at least about 30 to 60 minutes. This measure which is necessary because of the EDTA-induced unspecific interception of the free calcium ions can be dispensed with in the highly specific anticoagulation by means of rhirudin, which anticoagulation is less detrimental to the cells. The morphology of the nucleated cells in the hand-counted differential blood count was better preserved in rhirudin-anticoagulated blood than in the EDTA blood, in particular after a period of several hours.

The following test was performed:

Venous blood was taken from the cubital vein of a healthy test person (XM) and put into glass-made blood withdrawal tubes of the Vacutainer blood taking system (Becton and Dickinson). These tubes, which were not prepared by the manufacturer and were intended for the recovery of serum, had previously been loaded with heparin (5 IE/ml) or recombinant hirudin (200 ATU/ml). An EDTA blood count tube (Becton and Dickinson) which was also filled with venous native blood of the test person served as a control.

Four hours after the blood withdrawing operation (average transportation and dispatch time), the blood samples were evaluated by machine on the STKS of Coulter. The EDTA blood was additionally evaluated immediately after withdrawal. A partial blood count (numerical values) and a differential blood count were carried out by machine. Furthermore, smear preparations were made and the differential count was carried out manually under a microscope on the following day.

In summary, the blood samples could be evaluated on an equally good basis independently of the anticoagulant used. There were no essential differences in the numercial values in the partial blood count and in the manually performed differential blood counts. However, as regards differential blood counting by machine, a wrong measurement of part of the neutrophilic granulocytes, which were either recognized as basophilic granulocytes or as monocytes, could be observed, as expected, on the STKS device of Coulter which had been calibrated to EDTA blood, namely in the case of both heparin blood and hirudin blood. This wrong measurement is equally found in the known manner when EDTA blood is evaluated by machine within the first hour after blood drawing. This measurement error could be corrected by a corresponding operation.

4. Moreover, it could be shown that on the basis of the same rhirudin-treated blood withdrawal tubes of glass, and in addition to the already described tests, the blood group could be determined serologically, an antibody screening test could be performed, the Coombs tests could be carried out and erythrocyte concentrations could be tested. These tests could be carried out reliably and reproducibly. Technical problems did not arise. It should be emphasized that antibody screening tests, in particular, should be carried out with EDTA-free blood, if possible, to avoid interferences with complement-dependent antibodies, such as Kit a, Kit b, Lewis a and Lewis b.

The future in carrying out antibody screening tests and cross-matches of conserved blood, which are at the moment predominantly made manually on the basis of clotted blood by means of dropping techniques and by visually reading the agglutination, lies above all with large blood banks and hospitals in the automation of the pipetting and reading operations. Since in the case where conserved blood is cross-matched, both serum or plasma and erythrocytes are needed from the patient, the patient's blood must be anticoagulated and centrifuged when the cross-matching is to be carried out in an automated manner by means of an automatic pipetting device. Otherwise, blood clots would be aspirated upon removal of the centrifuged erythrocytes and the test would have to be interrupted. It is true that anticoagulation can be carried out with EDTA. EDTA-anticoagulated blood, however, is only suited to a certain degree for the performance of antibody screening tests, because EDTA interacts with complement, and complement-dependent antibodies such as Kit a and b, Lewis a and b might then no longer be detectable. By contrast, it could be shown for the first time that with rhirudin-anticoagulated blood, it was possible to carry out antibody screening tests and the cross-matching of blood in an automated manner and without any problems with the help of the automatic pipetting device ID-Sampler II using the Micro Typing Systems (both DiaMed AG, Cressier-sur-Morat, Switzerland).

The following tests could be carried out:

A: Manual Blood Group Typing and Manual Antibody Screening Test 5 ml venous whole blood from a healthy test person was introduced into a blood withdrawal tube of glass (Becton and Dickinson) which was untreated and had previously been loaded with recombinant hirudin (200 ATU/ml). After 30 minutes the blood in the untreated glass tube was completely clotted, whereas the hirudin-treated blood was anticoagulated. Both glass tubes were then centrifuged. Subsequently, the blood group was determined in both glass tubes, each time serologially by means of a manual dropping technique and visually reading the agglutination. Moreover, antibody screening tests were equally carried out with an antibody panel (screening) in three different media (0.9% NaCl, bromelin and Coombs).

In summary, rhirudin-anticoagulated blood could be used for determining the blood group and for antibody screening tests in the same manner as clotted blood (standard method).

B: Automatic Performance of Antibody Screening Tests by Means of the Automatic Pipetting Device ID-Sampler II Micro-Typing Systems, Company DiaMed AG, Cressier-sur-Morat, Switzerland 5 ml venous whole blood from a healthy test person was introduced into a blood withdrawal tube of glass (Becton and Dickinson) which had previously been loaded with recombinant hirudin (200 ATU/ml). The anticoagulated blood was centrifuged in the glass tube. The centrifuged blood withdrawal tubes was then put into the automatic pipetting device ID-Sampler II of DiaMed. In this automatic pipetting device plasma was then taken from the blood tube and pipetted into the corresponding Micro Typing Cards of DiaMed-ID, which were prepared for carrying out an antibody screening test in NaCL-, Coombs and cold media. These Micro Typing Cards were then incubated at 37° C. and subsequently centrifuged. For an exact identification of the samples the bar codes on the Micro Typing Cards were then entered manually by means of a bar code reader into a Compacq 4/50 PC. Finally, the Micro Typing Cards were put into the ID Reader M of DiaMed, agglutination was evaluated photooptically and printed out via the computer.

In summary, it could be shown that rhirudin-anticoagulated whole blood in the automatic pipetting device ID-Sampler II Micro Typing Systems of DiaMed could be used without any problems for automatically carrying out antibody screening tests.

Finally, it could be shown that the immunophenotype of normal and malign (leukemia, lymphoma) mononuclear cells will not change in human blood or bone marrow if the testing material is, in contrast to standard procedure, not anticoagulated by the addition of heparin, but is anticoagulated by the addition of rhirudin. The cell morphology in the rhirudin-anticoagulated blood or bone marrow was considerably better than in heparin blood (standard method) even after a storage time of 96 hours at room temperature (simulation of the transportation route in case of dispatch).

The following test was performed:

For immunophenotyping bone marrow blood (A) or peripheral blood (B), 5 ml material was respectively aspirated into a plastic syringe prepared with heparin (5 IE/ml) or recombinant hirudin (200 ATU/ml). Patient A is suffering from a carcinoma of the rectum. The test with his bone marrow had been carried out because of the suspected additional presence of acute myeloid leukemia. Patient B is suffering from chronic myeloid leukemia in a chronic phase. Testing on the basis of the peripheral blood was carried out for confirming the diagnosis. One hour (A) or three days (B) (simulation of the transportation route in the case of dispatch material, a frequent situation) after anticoagulabon at room temperature the material was centrifuged by a Ficoll gradient (company Pharmacia) and the mononuclear cells were thus separated. The mononuclear cells were then transferred by means of a pipette into a glass tube, the number of cells was determined on the Coulter counter and adjusted with 0.9% NaCl to a cell number of $5 \times 10^5$. Various primary antibodies were then pipetted to obtain fractions of this cell suspension. Following incubation and washing of the cell suspension a secondary fluorescence-labeled antibody (FITC-conjugated F $(ab')_2$ goat anti-mouse) was used for detecting the cell membrane-bound primary antibody (indirect immunofluorescence). The cell suspensions which had been treated with antibodies were then analyzed by flow cytometry (FACScan®, Becton and Dickinson). The numerical values correspond to the percentage of the fluorescent cells which were evaluated.

In summary, it becomes evident that both heparin-anticoagulated blood (standard method) and hirudin-anticoagulated blood can be analyzed immediately and also after three days in an equally good manner by immunophenotyping by means of FACScan®, and that such an analysis leads to comparable results, independently of the anticoagulation.

In summary, it could be shown for the first time that with the help of rhirudin-anticoagulated blood from a blood withdrawal tube a multitude of clinico-chemical routine and special tests (using the plasma) and also blood group-serological, cytomorphological and quantitative blood cell determinations (using the whole blood) are possible on an equal basis with the standard routine methods. In practice, the following possible improvements can be inferred therefrom:

1. Blood loss, in particular in seriously ill patients, which is caused by frequent diagnostic blood withdrawals, sometimes several times a day, can be considerably reduced.
2. Costs can considerably be reduced, due to the low purchasing and disposal costs of the blood withdrawal tubes and above all because of the possible integration of different diagnostic measurement and work places in laboratories with uniformly anticoagulated blood.

What is claimed is:

1. A method of determining clinico-chemical and hematological parameters on blood, comprising the steps of mixing a freshly taken blood sample with at least one direct, specific thrombin inhibitor and using said blood sample for determining both clinico-chemical parameters and hematological parameters, wherein the clinico-chemical parameters are selected from the group consisting of glutamine-oxaloacetic transaminase (GOT), glutamic-pyruvic transaminase (GPT), alkaline phosphatase, amylase, lipase, γ-glutamyl transferase (GGT), lactate dehydrogenase (LDH), creatine kinase, liver enzymes, cholinesterase, α-hydroxybutyrate dehydrogenase (α-HBDH); creatinine, urea, uric acid, bilirubin, glucose, total cholesterol, triglycerides; sodium, potassium, chloride, magnesium, phosphate, calcium; coagulation parameters C3, C4 and quick prothrombin time; β-human chorionic gonadotropin (β-HCG), T3, T4, and TSH basal hormones; iron, transferrin, hemoglobin, total protein, protein electrophoresis, albumin, C-reactive protein, immunoglobulins, antistreptolysin titer, rheumatoid factors, apolipoprotein, digitoxin, vancomycin, theophylline, and osmolality, and the hematological parameters are selected from the group consisting of erythrocyte, leukocyte and thrombocyte counts, leukocyte fraction of nucleated blood cells (differential count), antigenicity of blood cells, immunophenotyping of mononuclear cells, antibody screening tests, Coombs test, and blood sedimentation rate.

2. A method according to claim 1, wherein hirudin, desulfatohirudin or both are used as the at least one thrombin inhibitor.

3. A method according to claim 2, wherein recombinant hirudin, desulfatohirudin or both are used.

4. A method according to claim 1 wherein cellular and corpuscular components are removed from the blood sample prior to the determination of the clinico-chemical parameters.

5. A method according to claim 1, wherein the hematological parameters comprise erythrocyte, leukocyte and thrombocyte counts, or differential blood count or both.

6. A method according to claim 1, wherein the hematological parameters comprise antigenicity of blood cells, antibody screening tests, Coombs tests or any combination thereof.

7. A method according to claim 1, wherein one of the hematological parameters comprises an immunophenotyping operation which is carried out with the freshly taken blood sample obtained from peripheral blood or bone marrow blood.

8. A method according to claim 1, wherein the freshly taken blood sample is put into a container containing the at least one thrombin inhibitor.

9. A method according to claim 1, wherein the parameters are determined in automated measuring devices.

10. A method for determining clinico-chemical blood parameters, comprising the steps of mixing a freshly taken blood sample with an anticoagulant consisting essentially of at least one specific, direct thrombin inhibitor and determining the clinico-chemical parameters using the resulting blood sample, wherein said clinico-chemical blood parameters are selected from the group consisting of glutamine-oxaloacetic transaminase (GOT), glutamic-pyruvic transaminase (GPT), alkaline phosphatase, amylase, lipase, γ-glutamyl transferase (GGT), lactate dehydrogenase (LDH), creatine kinase, liver enzymes, cholinesterase, α-hydroxybutyrate dehydrogenase (α-HBDH); creatinine, urea, uric acid, bilirubin, glucose, total cholesterol, triglycerides; sodium, potassium, chloride, magnesium, phosphate, calcium; coagulation parameters C3, C4 and quick prothrombin time; β-human chorionic gonadotropin (β-HCG), T3, T4, and TSH basal hormones; iron, transferrin, hemoglobin, total protein, protein electrophoresis, albumin, C-reactive protein, immunoglobulins, antistreptolysin titer, rheumatoid factors, apolipoprotein, digitoxin, vancomycin, theophylline, and osmolality.

11. A method according to claim 10, wherein cellular and corpuscular components are removed from the blood sample prior to the determination of the clinico-chemical parameters.

12. A method according to claim 10, wherein hirudin, desulfatohirudin or both are used as the at least one thrombin inhibitor.

13. A method according to claim 12, wherein recombinant hirudin, recombinant desulfatohirudin or both are used.

14. A method according to claim 10, wherein the freshly taken blood sample is put into a container containing the at least one thrombin inhibitor.

15. A method according to claim 10, wherein the clinico-chemical parameters are determined in automated measuring devices.

16. A method according to claim 10 wherein the clinico-chemical blood parameters are determined using blood plasma.

17. A method of using blood withdrawal containers containing at least one direct, specific thrombin inhibitor, comprising collecting blood in said containers and determining both clinico-chemical and hematological parameters, wherein the clinico-chemical parameters are selected from the group consisting of glutamine-oxaloacetic transaminase (GOT), glutamic-pyruvic transaminase (GPT), alkaline phosphatase, amylase, lipase, γ-glutamyl transferase (GGT), lactate dehydrogenase (LDH), creatine kinase, liver enzymes, cholinesterase, α-hydroxybutyrate dehydrogenase (α-HBDH); creatinine, urea, uric acid, bilirubin, glucose, total cholesterol, triglycerides; sodium, potassium, chloride, magnesium, phosphate, calcium; coagulation parameters C3, C4 and quick prothrombin time; β-human chorionic gonadotropin (β-HCG), T3, T4, and TSH basal hormones; iron, transferrin, hemoglobin, total protein, protein electrophoresis, albumin, C-reactive protein, immunoglobulins, antistreptolysin titer, rheumatoid factors, apolipoprotein, digitoxin, vancomycin, theophylline, and osmolality, and the hematological parameters are selected from the group consisting of erythrocyte, leukocyte and thrombocyte counts, leukocyte fraction of nucleated blood cells (differential count), antigenicity of blood cells, immunophenotyping of mononuclear cells, antibody screening tests, Coombs test, and blood sedimentation rate.

18. The method of claim 17, wherein the blood withdrawal containers are coated with said at least one thrombin inhibitor.

19. A method of using blood withdrawal containers containing an anticoagulant consisting essentially of at least one direct, specific thrombin inhibitor, comprising collecting blood in said containers and determining clinico-chemical parameters, wherein the clinico-chemical parameters are selected from the group consisting of glutamine-oxaloacetic transaminase (GOT), glutamic-pyruvic transaminase (GPT), alkaline phosphatase, amylase, lipase, γ-glutamyl transferase (GGT), lactate dehydrogenase (LDH), creatine kinase, liver enzymes, cholinesterase, α-hydroxybutyrate dehydrogenase (α-HBDH); creatinine, urea, uric acid, bilirubin, glucose, total cholesterol, triglycerides; sodium, potassium, chloride, magnesium phosphate, calcium; coagulation parameters C3, C4 and quick prothrombin time; β-human chorionic gonadotropin (β-HCG), T3, T4, and TSH basal hormones; iron, transferrin, hemoglobin, total protein, protein electrophoresis, albumin, C-reactive protein, immunoglobulins, antistreptolysin titer, rheumatoid factors, apolipoprotein, digitoxin, vancomycin, theophyllin, and osmolality.

20. The method of claim 17 or 19, wherein the at least one thrombin inhibitor is selected from the group consisting of hirudin, desulfatohirudin and both hirudin and desulfatohirudin.

21. The method of claim 19, wherein the at least one thrombin inhibitor is selected from the group consisting of recombinant hirudin, recombinant desulfatohirudin and both recombinant hirudin and recombinant desulfatohirudin.

* * * * *